United States Patent [19]

Yamamoto

[11] Patent Number: 5,800,806
[45] Date of Patent: Sep. 1, 1998

[54] DEODORANT POROUS POLYMER AND A DEODORANT FIBROUS MATERIAL USING THE SAME

[76] Inventor: Tohru Yamamoto, c/o Nakato Laboratory, Inc. 6, Ohshinohara, Yasu-cho, Yasu-gun, Shiga-ken, Japan

[21] Appl. No.: 368,538

[22] Filed: Jan. 4, 1995

Related U.S. Application Data

[62] Division of Ser. No. 962,893, Oct. 19, 1992, Pat. No. 5,405,687, which is a division of Ser. No. 581,331, Sep. 11, 1990, Pat. No. 5,185,169.

[51] Int. Cl.$^6$ .............................. A61K 6/00; A61K 7/00; A61L 9/00; A61L 9/01
[52] U.S. Cl. .............................. 424/76.1; 424/401
[58] Field of Search .................. 424/401, 65, 635, 424/600, 691, 722, 76.3, 76.5; 428/261

[56] References Cited

U.S. PATENT DOCUMENTS 4,937,208  6/1990  Yamamoto ........................ 501/12
4,988,505  1/1991  Watanabe et al. .................. 424/76.3

FOREIGN PATENT DOCUMENTS 403130468A  8/1989  Japan.
403262529A  3/1990  Japan.

*Primary Examiner*—Thurman K. Page
*Assistant Examiner*—Sharon Howard
*Attorney, Agent, or Firm*—Morrison & Foerster LLP

[57] ABSTRACT

A deodorant porous polymer having excellent deodorant effects is provided. The deodorant porous polymer is in the shape of substantially uniform particulates or an aggregate thereof, and is obtained by the hydrolysis and polycondensation of at least one alkoxide selected from the group consisting of inorganic alkoxides and metal alkoxides through the use of a sol-gel method. Also provided is a deodorant fibrous material that includes a fibrous substrate and a deodorant porous polymer as mentioned above, which is combined with the fibrous substrate in the physically-combined state and/or the chemically-combined state.

3 Claims, No Drawings

DEODORANT POROUS POLYMER AND A DEODORANT FIBROUS MATERIAL USING THE SAME

This application is a division of application Ser. No. 07/962,893 filed Oct. 19, 1992, now U.S. Pat. No. 5,405,687, which is a divisional of Ser. No. 07/581,331 filed Sep. 11, 1990, which is now U.S. Pat. No. 5,185,169.

BACKGROUND OF THE INVENTION

1. Field of the Invention

This invention relates to a deodorant polymer, and more particularly, to a porous polymer having excellent deodorant effects which is obtained by the hydrolysis and polycondensation of inorganic alkoxides and/or metal alkoxides by a sol-gel method. This invention also relates to a deodorant fibrous material obtained by combining such a deodorant porous polymer with a fibrous substrate.

2. Description of the Prior Art

In recent years, with the improvements in the standard of living, there have been strong demands to remove any displeasing odors in order to live a comfortable life. For example, various deodorizers are used in order to remove or mask an odor in places with high airtightness, such as bathrooms, toilets, cars, and refrigerators.

Among the deodorizers, those having strong odors themselves such as perfumes or balsams are often used to mask an odor in places with high airtightness, such as toilets and cars. However, these deodorizers are limited to specific applications because of their own strong smells. On the other hand, there are chemical deodorizers that deodorize by chemical decomposition of odoriferous compounds. Such deodorizers usually contain, as the main component, a substance extracted from plants or synthetic compound, and used, for example, in a spray, for chemically decomposing a bad smell of trash or deodorizing body odor. However, these chemical deodorizers have the disadvantages of having smell themselves and the capability to decompose only specific odors.

Other deodorizers include absorptive deodorizers such as, active carbon and silica gel. These deodorizers are composed of porous particles in which odors are adsorbed, thereby achieving deodorization. Silica gel used as a moisture absorbent can also show deodorant effects. Powders of silica gel manufactured by a conventional method, however, have large pore sizes and the porosity (the proportion of pores to the total volume) is relatively small, thereby making it impossible to obtain satisfactory deodorant effects. Even when active carbon with a relatively large deodorizing activity is used, it is impossible to obtain satisfactory deodorant effects, because the pore size is not uniform and the particle size is relatively large.

Recently, attempts have been made to give deodorant effects to fibrous materials such as insoles, sanitary items, and underclothes. In a method for producing such deodorant fibrous materials, for example, thin layers of deodorant powders are sealed into a cloth of fibrous materials. However, the product obtained by this method is bulky and cannot be used for underclothes and the like. A preferable method for producing deodorant fibrous materials is to combine deodorant materials with a fibrous substrate. However, active carbon which is believed to have the highest deodorant activity has a black-colored appearance, and therefore, the applications of active carbon are limited. As described above, deodorant fibrous materials having excellent deodorant effects which can be readily produced are not yet obtainable.

SUMMARY OF THE INVENTION

The deodorant porous polymer of this invention, which overcomes the above-discussed and numerous other disadvantages and deficiencies of the prior art, is a porous polymer in the shape of substantially uniform particulates or an aggregate thereof, which is obtained by the hydrolysis and polycondensation of at least one alkoxide selected from the group consisting of inorganic alkoxides and metal alkoxides through the use of a sol-gel method.

The method for producing a deodorant porous polymer of this invention comprises the step of hydrolyzing and polycondensing at least one alkoxide selected from the group consisting of inorganic alkoxides and metal alkoxides by the use of catalyst for a sol-gel method so as to obtain a porous polymer in the shape of substantially uniform particulates or an aggregate thereof.

In a preferred embodiment, the aforementioned catalyst for the sol-gel method is a base catalyst.

The deodorant fibrous material of this invention comprises a fibrous substrate and a deodorant porous polymer in the shape of substantially uniform particulates or an aggregate thereof the porous polymer being prepared from at least one alkoxide selected from the group consisting of inorganic alkoxides and metal alkoxides and a silane coupling agent through the use of a sol-gel method, and the porous polymer being combined with the fibrous substrate in the physically-combined state and/or the chemically-combined state.

In a preferred embodiment, the aforementioned silane coupling agent has an epoxy group.

The method for producing a deodorant fibrous material of this invention comprises the steps of preparing the composition containing at least one alkoxide selected from the group consisting of inorganic alkoxides and metal alkoxides, a silane coupling agent, a catalyst for a sol-gel method, and a solvent, impregnating a fibrous substrate with said composition in a sol state, and converting said composition into a gel state to form a porous polymer.

In a preferred embodiment, the aforementioned catalyst for the sol-gel method comprises an acid catalyst and a base catalyst.

In a more preferred embodiment, the aforementioned base catalyst for the sol-gel method is a tertiary amine which is substantially insoluble in water and soluble in organic solvents.

In a more preferred embodiment, the aforementioned silane coupling agent has an epoxy group.

Thus, the invention described herein makes possible the objectives of (1) providing a deodorant porous polymer having excellent deodorant effects; (2) providing a method for readily producing such a deodorant porous polymer; (3) providing a deodorant fibrous material in which a deodorant porous polymer having excellent deodorant effects as mentioned above is strongly combined with a fibrous substrate; and (4) providing a method for readily producing such a deodorant fibrous material.

DESCRIPTION OF THE PREFERRED EMBODIMENTS

The inorganic or metal alkoxides which can be used in this invention are expressed by the general formula M(OR)m, where M is an inorganic atom, such as Li, Na, Cu, Mg, Ca, Sr, Ba, Zn, B, Al, Ga, Y, Si, Ge, Pb, P, Sb, Ta, W, La, Nd, and Ti; R is a lower alkyl containing one to four carbon atoms; and m is a valence number of M. Specific examples of the alkoxides includes $Si(OC_2H_5)_4$, $Al(O-iso-C_3H_7)_3$, Ti(O-iso-$C_3H_7$)$_4$, Zr(O-n-$C_3H_7$)$_4$, Zr(O-t-$C_4H_9$)$_4$, Zr(O-n-$C_4H_9$)$_4$, Ca(O$C_2H_5$)$_2$, Fe(O$C_2H_5$)$_3$, V(O-iso-$C_3H_7$)$_4$, Sn(O-t-$C_4H_9$)$_4$, Li(O$C_2H_5$), Be(O$C_2H_5$)$_3$, B(O$C_2H_5$)$_3$, P(O$C_2H_5$)$_3$, P(O$CH_3$)$_3$, Mg(O$CH_3$)$_2$, and Mg(O$C_2H_5$)$_2$. Alkoxides containing two kinds of metals, such as Mg[Al(iso-O$C_3H_7$)$_4$]$_2$ and Ni[Al(iso-O$C_3H_7$)$_4$]$_2$, can also be used. Particularly, Si(O$C_2H_5$)$_4$, Ca(O$C_2H_5$)$_2$, Zr(O-t-$C_4H_9$)$_4$, Zr(O-n-$C_4H_9$)$_4$, and Mg(O$C_2H_5$)$_2$ are preferred. Two or more kinds of these alkoxides can be used as a mixture. Particularly, it is preferred to use calcium alkoxide and/or magnesium alkoxide together with other alkoxide, for example, silane alkoxide. The deodorant porous polymer of this invention can adsorb both acid and alkali substances effectively. In cases where calcium alkoxide or magnesium alkoxide is used, acid substances are more readily adsorbed, because the Ca- or Mg-containing portion of the porous polymer obtained acts as a Brønsted base or a Lewis base.

The silane coupling agent used in this invention, if needed, can be any of the well-known silane coupling agents, such as (γ-glycidoxypropyl)trimethoxysilane, (γ-glycidoxypropyl)-methyldiethoxysilane, β-(3,4-epoxycyclohexyl)ethyltrimethoxysilane, vinyltrimethoxysilane, vinyltrichlorosilane, vinyltris(β-methoxyethoxy)silane, vinyltriacetoxysilane, (γ-methacryloxypropyl)trimethoxysilane, N-β-(N-vinylbenzylaminoethyl)-γ-aminopropyltrimethoxysilane hydrochloride, γ-aminopropyltriethoxysilane, N-phenyl-γ-aminopropyltrimethoxysilane, γ-(2-aminoethyl) aminopropyltrimethoxysilane, γ-(2-aminoethyl) aminopropylmethyldimethoxysilane, γ-mercaptopropyltrimethoxysilane, γ-mercaptopropylmethyldimethoxysilane, methyltrimethoxysilane, methyltriethoxysilane, hexamethyldisilazane, γ-anilinopropyltrimethoxysilane, γ-chloropropyltrimethoxysilane, γ-chloropropylmethyldimethoxysilane, methyltrichlorosilane, dimethyldichlorosilane, trimethylchlorosilane, octadecyldimethyl[3-(trimethoxysylil)propyl]ammonium-chloride, and a mixture of aminosilanes.

Particularly, in cases where deodorant porous polymers are prepared, silane coupling agents containing epoxy or vinyl groups are preferred. In cases where deodorant fibrous materials are prepared, silane coupling agents containing epoxy or vinyl groups are also preferred. The amount of silane coupling agent to be used is not more than 10 parts by weight, and more preferably, about 3 parts by weight, for every 100 parts by weight of the aforementioned alkoxide. In cases where deodorant fibrous materials are prepared, it is desirable to use 1 to 10 parts by weight of silane coupling agent, and more preferably, about 3 parts by weight of silane coupling agent, for every 100 parts by weight of the aforementioned alkoxide. When the silane coupling agent is used in an amount of more than 10 parts by weight, the rigidity of the deodorant porous polymer obtained increases. Therefore, for example, when combining the deodorant porous polymer with a fibrous substrate, the flexibility of the fibers is decreased. In cases where deodorant fibrous materials are prepared, when the amount of silane coupling agent to be added is less than 1 part by weight, the combined strength is decreased and the amount of deodorant porous polymer is prone to decrease. When silane coupling agents containing vinyl groups are used, irradiation with electron beams is required during the production process.

In order to produce the deodorant porous polymer of this invention, an acid catalyst is used, if necessary, as a catalyst for the sol-gel method. As the acid catalyst, an inorganic acid such as hydrochloric acid, sulfuric acid, or nitric acid is usually used. It is possible to obtain the same effects by bubbling a hydrogen chloride gas into the reaction solution. Organic acids or their anhydrides can also be used. Examples thereof include tartaric acid, phthalic acid, maleic acid, dodecylsuccinic acid, hexahydrophthalic acid, methyl endic acid, pyromellitic acid, benzophenonetetracarboxylic acid, dichlorosuccinic acid, chlorendic acid, phthalic anhydride, maleic anhydride, dodecylsuccinic anhydride, hexahydrophthalic anhydride, methyl endic anhydride, pyromellitic dianhydride, benzophenonetetracarboxylic anhydride, dichlorosuccinic anhydride, and chlorendic anhydride. For every mole of the aforementioned alkoxide, 0.5 mol or less of these acids are used. In cases where deodorant fibrous materials are prepared, 0.001 mol or more of these acids, preferably 0.003–0.005 mol of these acids, are used for every mole of the aforementioned alkoxide. If the amount of the acid is too large, the polycondensation of the alkoxides proceeds too far and the polymer particles become too large, and the pore size of the polymer particles become large because of a high degree of crosslinking, thereby deteriorating the deodorant effects of the polymer particles.

The base catalyst for the sol-gel method employed in this invention can be either an inorganic base or an organic base. Examples of the inorganic base catalyst includes potassium hydroxide, sodium hydroxide, lithium hydroxide, rubidium hydroxide, magnesium hydroxide, and ammonia. Examples of the organic base catalyst includes primary amines, secondary amines, tertiary amines, polyamines, and complex compounds of amines, such as ethylenediamine, diethylenetriamine, ethanolamine, butylamine, triethylenetetramine, diethylaminopropylamine, N-aminoethylpiperazine, N,N-dimethylbenzylamine, tripropylamine, tributylamine, tripentylamine, tris (dimethylaminomethyl)phenol, methaphenylenediamine, diaminodiphenylmethane, diaminodiphenylsulfone, polyamide resins, dicyandiamide, boron trifluoride-monoethylamine complexes, menthanediamine, xylylenediamine, and ethylmethylimidazole.

Among the aforementioned base catalysts, a porous polymer in the shape of particulates can be obtained by the use of ammonia, particularly an ammonia gas. More preferred is a tertiary amine that is substantially insoluble in water and soluble in organic solvents. Examples of the tertiary amines which can be used as a base catalyst include N,N-dimethylbenzylamine, tripropylamine, tributylamine, and tripentylamine, with N,N-dimethylbenzylamine being particularly preferred.

The amount of base catalyst to be used is in the range of from 0.002 to 1.5 mol for every mole of the alkoxide. In cases where the aforementioned tertiary amine that is substantially insoluble in water and soluble in organic solvents is used, the amount thereof is 0.002 mol or more, and more preferably in the range of from 0.004 to 0.008 mol, for every mole of the alkoxide. In other cases, the base catalyst is usually used in an amount of from 0.1 to 1.5 mol.

As a solvent that can be used in the production of a deodorant porous polymer, there is a mixture of water (used in hydrolysis) and an organic solvent that can be miscible with water or an organic solvent that can be partly dissolved in water. Examples of the organic solvents include methanol, ethanol, butanol, propanol, pentanol, hexanol, acetone, methyl ethyl ketone, and formamide. The amount of water to be used is 10 mol or less, preferably 1 to 10 mol, more preferably 1 to 6 mol, and still more preferably about 4 mol, for every mole of the alkoxide. If there is too little water, the hydrolysis of the alkoxide proceeds slowly and the polycondensation is retarded. However, the hydrolysis proceeds gradually with water present in the air, so it is not necessary to add water to the solvent. Particularly, in cases where zirconium-containing alkoxides having a higher moisture absorption are used, it is not necessary to add water. If there is too much water, the deodorant effects of the deodorant porous polymer obtained will be decreased.

In order to produce a deodorant porous polymer according to the method of this invention, the inorganic alkoxide and/or the metal alkoxide are mixed with a solvent. The concentration of alkoxide is preferably in the range of from 300 to 500 g/l. To this mixture, an acid catalyst for the sol-gel method is added, if needed. However, the aforementioned acid catalyst is not necessarily added, because as the mixture is vigorously stirred, carbonic acid is produced by incorporation of carbon dioxide present in the air into the mixture. With this treatment, hydrolysis is substantially complete. Then, a base catalyst for the sol-gel method is added to this mixture. Although this mixture is either a sol mixture or an emulsion, gelation occurs as the polycondensation reaction of the hydrolyzed product proceeds by the aid of the base catalyst. The period of gelation can be in the range of from several seconds to hours by adjusting the amount of the base catalyst. It is also possible to proceed the reaction by mixing the alkoxide, the catalyst for the sol-gel method, and the solvent at the same time. If needed, silane coupling agents can be added to the mixture together with the alkoxide. Particularly, in cases where the deodorant porous polymer is combined with a fibrous substrate, plastic substrate, or the like, the addition of silane coupling agents is preferred.

The porous polymer of this invention is prepared as follows. With the use of the aforementioned sol mixture or emulsion (including precipitates), or alternatively a gel. When using a gel, a deodorant porous polymer in the shape of particulates is obtained after grinding and heating to dewater the gel. When using a sol mixture, the period of gelation is preferably set to be about 5 hours by adjusting the pH of the mixture to about 6–8 and using a small amount of base catalyst. For example, a deodorant porous polymer in the shape of particulates is obtained by spray drying or freeze drying of the sol mixture. It is also possible to use a precipitation method or an evaporating decomposition method. In addition, the aforementioned mixture in the sol state can be formed into a film by drying and removing the solvent. The film obtained is cut into appropriate sizes to use as a deodorant film. This film, like the aforementioned polymer in the shape of particulates, is porous and has excellent deodorant effects.

The deodorant porous polymer of this invention can be used in the shape of particulates as mentioned above. Moreover, the deodorant porous polymer can be combined with various kinds of films, fibrous materials, plastic materials, timbers and the like, as a substrate. In a preferred method for combining various materials with the deodorant porous polymer of this invention, the aforementioned mixture in the sol state is applied to the substrate or, the substrate is impregnated with the aforementioned mixture in the sol state, followed by drying the substrate. For example, a deodorant fibrous material is produced as follows:

The fibrous substrate used for the deodorant fibrous materials can be made of natural fiber, artificial fiber, or semi-artificial fiber. More specifically, fibrous materials such as fabric, nonwoven fabric, thread, and paper can be used as the fibrous substrate. Alternatively, fibrous materials such as unspun cotton can be used as the fibrous substrate.

In order to produce a deodorant fibrous materials according to the method of this invention, a composition containing alkoxides, a silane coupling agent, a catalyst for the sol-gel method, and a solvent is first prepared as a mixture in the sol state. The concentration of the alkoxide in the mixture is preferably in the range of from 200 to 300 g/l. When this mixture is left as it is, the hydrolysis of alkoxide, the polycondensation of the hydrolyzed product, and the reaction of the hydrolyzed product with the silane coupling agent proceed, resulting in a gelation. The time until gelation is completed (i.e., gelation time) depends on the amount of water used, the amount of catalyst for the sol-gel method, and the pH of the composition. It is preferred to adjust the pH to about 4–5 so that the gelation time becomes approximately 5 hours.

Next, the fibrous substrate is impregnated with the aforementioned composition in the sol state. Impregnation of the fibrous substrate can be achieved by immersing the fibrous substrate in a tank filled with the sol mixture or by spraying the sol mixture onto the fibrous substrate, followed by passing the substrate through a mangle. Preferably, this process is repeated several times, thereby sufficiently impregnating the fibrous substrate with the sol mixture. When silane coupling agents containing vinyl groups are present in the sol mixture, the fibrous substrate impregnated with the sol mixture is irradiated during the production process.

By leaving this fibrous substrate in the air, the gelation of the mixture occurs to form a porous polymer, resulting in a deodorant fibrous material in which the porous polymer is combined with the fibrous substrate.

In the method of this invention, alkoxide is hydrolyzed by the aid of an acid catalyst (i.e., alkoxy groups are converted into hydroxyl groups), and the hydrolyzed alkoxides cause polycondensation with each other by the aid of a base catalyst, thereby forming a polymer. When a silane coupling agent is used together with alkoxides, the inorganic portion of the silane coupling agent is hydrolyzed (i.e., alkoxy groups are converted into hydroxyl groups) and cause polycondensation with the hydrolyzed alkoxides. When the silane coupling agent contains epoxy groups, the cleavage of the epoxy groups occurs, and the polycondensation reaction proceeds between the hydroxyl groups produced and the hydrolyzed alkoxides. In the method of this invention, since the condensation reaction proceeds in a uniform solution and a small amount of catalyst is used, the polymer particles obtained (i.e., primary particulates) has a small particle diameter and their size is uniform. These primary particulates have fine pores of 40 to 200 angstroms and the size of the particles is in the range of from 10 to 15 nm. As the polycondensation proceeds, the particles combine with each other, thereby forming polymer particles with a three-dimensional structure (i.e., secondary particulates). The porosity of the polymer particles is about 60%. The porous polymer thus formed has a uniform particle diameter and the adsorbing surface area in the pores of the polymer particles and in the spaces formed between the particles is several times larger than that of active carbon, thereby making it possible to efficiently adsorb odor substances. Therefore, the porous polymer has excellent deodorant effects.

The deodorant porous polymer of this invention can effectively adsorb both acid and alkaline substances. When calcium alkoxide or magnesium alkoxide is used, acid substances are more readily adsorbed, because the Ca- or Mg-containing portion of the porous polymer obtained acts as a Brønsted base or a Lewis base. Therefore, a substance such as isovaleric acid which is particularly difficult to be adsorbed by silica gel or active carbon can be readily adsorbed.

In the deodorant fibrous material of this invention, the fibrous substrate is impregnated with the sol mixture and the polymer particles as mentioned above are formed in the fibrous substrate. Therefore, the polymer particles permeate inside of the fibrous substrate and combine strongly with the fibrous substrate in a physically-combined state. Furthermore, protons of hydroxyl groups in the fibrous substrate are taken away by the action of the catalyst in forming the polymer. Therefore, the polymer particles and the fibrous substrate are chemically combined with each other through an oxygen bond. Particularly, when the polymer particles are formed using a silane coupling agent, the polymer particles readily combine with the fibrous substrate, since the compatibility of the organic portion of the silane coupling agent with the fibrous material is relatively high. Some fibrous materials (e.g., polyamide fibers and glass fibers) have a possibility that the fiber molecules may react to combine chemically with the hydrolyzed alkoxides, the silane coupling agent, and the cleaved epoxy groups. Since the porous polymer is strongly combined with the fibrous substrate in the physically-combined state and/or the chemically-combined state, the deodorant fibrous material of this invention has no tendency for the porous polymer to drop. In addition, the softness and flexibility of the fibrous substrate is not substantially affected. Furthermore, since the porous polymer is colorless, it is possible to give deodorant effects without affecting the color and pattern of the fibrous substrate.

As described above, the deodorant porous polymer of this invention has excellent deodorant effects and can be readily prepared by the sol-gel method. In addition, the deodorant fibrous material obtained by combining this deodorant porous polymer with a fibrous substrate has excellent deodorant effects and no tendency for the porous polymer to drop. Therefore, the deodorant fibrous material of this invention can be widely used for deodorant products, such as curtains, carpets, car interiors, insoles, sanitary items, and underclothes.

The invention will be further explained with reference to the following examples.

EXAMPLE 1

The components shown in Table 1, except N,N-dimethylbenzylamine, were mixed with stirring, thereby obtaining a suspension of ethylsilicate. N,N-dimethylbenzylamine was added to this suspension with stirring.

TABLE 1

| Components | Amount (wt %) |
| --- | --- |
| Ethylsilicate | 42.28 |
| Ethanol | 39.29 |
| Water | 14.61 |
| N,N-dimethylbenzylamine | 3.82 |

By leaving the reaction mixture for 2 hours, porous monodisperse particulates were produced and these particulates gathered to form a precipitate. The precipitate was filtered and dewatered, thereby obtaining a porous polymer in the shape of particulates. The particulates thus obtained have an average particle diameter of 200 nm and are porous particles having pores with a diameter of approximately 200 angstroms.

The porous polymer was examined for deodorant effects on trimethylamine, ammonia, and isovaleric acid. The results are shown in Table 4, together with the results obtained in Examples 2 to 4, and Comparative Example 1.

[Deodorant Test Using Trimethylamine]

First, 20 g of the deodorant porous polymer is placed in an airtight container of 350 ml, and 1 ml of 1.5% aqueous trimethylamine solution is added thereto. The container is made airtight and left for 1 hour. Then, 1 ml of gas in the airtight container is taken out and subjected to a gas chromatography analysis, by which the peak area corresponding to trimethylamine is determined.

The same procedure is repeated, as a control, except that the deodorant porous polymer is not used. The peak area corresponding to trimethylamine obtained in this procedure is taken as 100% and the peak area corresponding to trimethylamine obtained by using the aforementioned deodorant porous polymer is calculated. The rate of peak area decrease is determined as the rate of trimethylamine adsorption with respect to the test polymer.

[Deodorant Test Using Ammonia]

First, 20 g of the deodorant porous polymer is placed in an airtight container of 350 ml, 1 ml of 0.5% aqueous ammonia solution is added thereto. The container is made airtight and left for 1 hour. Then, 10 ml of gas in the airtight container is taken out and bubbled into 10 ml of aqueous boric acid solution so as to be absorbed thereby. The absorbance at 630 nm is measured by an indophenol method to determine the amount of ammonia in the solution.

The same procedure is repeated, as a control, except that the deodorant porous polymer is not used. The amount of ammonia obtained in this procedure is taken as 100% and the percentage of the ammonia concentration obtained by using the aforementioned deodorant porous polymer is calculated. The rate of ammonia concentration decrease is determined as the rate of ammonia adsorption with respect to the test polymer.

[Deodorant Test Using Isovaleric Acid]

First, 20 g of the deodorant porous polymer is placed in an airtight container of 350 ml, and 5 µl of isovaleric acid is added thereto. The container is made airtight and left for 1 hour in a thermostat at 50° C. Then, 1 µl of gas in the airtight container is taken out and subjected to a gas chromatography analysis, by which the peak area corresponding to isovaleric acid is determined.

The same procedure is repeated, as a control, except that the deodorant porous polymer is not used. The peak area corresponding to isovaleric acid obtained in this procedure is taken as 100% and the corresponding to isovaleric acid obtained by using the aforementioned deodorant porous polymer is calculated. The rate of peak area decrease is determined as the rate of isovaleric acid adsorption with respect to the test polymer.

EXAMPLE 2

The same procedure was repeated as in Example 1, except that aqueous ammonia solution (28%) was used instead of N,N-dimethylbenzylamine. The porous polymer in the shape of particulates similar to that obtained in Example 1 was obtained.

EXAMPLE 3

Among the components shown in Table 2, ethylsilicate and ethanol was mixed. The amount of water shown in Table 2 was added dropwise to the solution, while adjusting the rate of addition so that the solution did not become cloudy. Ammonia gas was bubbled into the mixture so that the amount of ammonia shown in Table 2 was added thereto. The mixture was sprayed on a plastic film as liquid drops of approximately 10 to 20 nm by the use of a spray. The film was dried while heating to about 30°–70° C., so that the fine powders (porous polymer) remained on the film. These porous polymer particulates have a similar structure to that of the porous polymer particulates obtained in Example 1. The particulates were collected and evaluated in the same manner as in Example 1. The results of the deodorant tests are shown in Table 4.

TABLE 2

| Components | Amount (wt %) |
|---|---|
| Ethylsilicate | 42.28 |
| Ethanol | 40.01 |
| Water | 14.61 |
| Ammonia | 3.10 |

EXAMPLE 4

The components shown in Table 3, except N,N-dimethylbenzylamine, were mixed with stirring, thereby obtaining a suspension containing ethylsilicate and calcium methoxide. N,N-dimethylbenzylamine was added to the suspension with stirring, and the gelation of the mixture occurred in about 10 minutes.

TABLE 3

| Components | Amount (wt %) |
|---|---|
| Ethylsilicate | 42.28 |
| Ethanol | 37.91 |
| 2N hydrochloric acid | 0.17[a] |
| Water | 14.61 |
| Calcium methoxide | 1.21 |
| Ethanol solution of N,N-dimethylbenzylamine (3.2 wt %) | 3.82 |

[a] In terms of the amount of HCl

The mixture in the soft-gel state was ground and dried, thereby obtaining powders having an average particle diameter of 1.85 μm. The deodorant effects were evaluated in the same manner as in Example 1. The results are shown in Table 4.

Comparative Example 1

The same procedure was repeated as in Example 1, except that active carbon was used instead of the deodorant porous polymer. The results of the deodorant tests are shown in Table 4.

TABLE 4

| | Rate of odor substance adsorption (%) | | |
|---|---|---|---|
| Example No. | Trimethylamine | Ammonia | Isovaleric acid |
| Example 1 | 99.9 | 98.8 | 90.8 |
| Example 2 | 99.9 | 96.4 | 92.3 |
| Example 3 | 99.9 | 99.6 | 89.4 |
| Example 4 | 99.9 | 98.7 | 96.5 |
| Comparative Example 1 | 3.0 | 14.8 | — |

EXAMPLE 5

The components shown in Table 5 were mixed with stirring, thereby obtaining a mixture in the sol state.

Next, a cuprammonium rayon cloth (62.6 g/m$^2$) was immersed in the aforementioned mixture, followed by passing the cloth through a mangle. This process was repeated twice, thereby sufficiently impregnating the mixture into the cloth. Next, this cloth was dried at 130° C. for 5 minutes, thereby obtaining a cloth in which the components of the aforementioned mixture were contained at ratio of 11 g/m$^2$ (solid content).

TABLE 5

| Components | Amount (wt %) |
|---|---|
| Ethylsilicate | 20.22 |
| Ethanol | 20.22 |
| 2-N hydrochloric acid | 0.14 |
| Water | 6.90 |
| γ-Glycydoxy propylmethoxysilane (Toray Silicon SH 6040) | 3.16 |
| Methanol | 47.46 |
| Ethanol solution of N,N-dimethylbenzylamine (3.2 wt %) | 1.90 |

The dried cloth was cut into 15×20 cm swatches as a test piece of deodorant fibrous material. This test piece was used instead of a porous polymer, and the deodorant effects on trimethylamine, ammonia, and isovaleric acid were evaluated, in the same manner as in Example 1. In each test, an untreated cloth was used as a control. The results are shown in Table 6, together with the results obtained in Examples 6 and 7, and Comparative Example 2.

EXAMPLE 6

The same procedure was repeated as in Example 5, except that a polyester cloth (64.2 g/m$^2$) was used as a fibrous substrate, thereby obtaining a deodorant fibrous material in which a porous polymer was combined with the fibrous substrate at the rate of 10 g/m$^2$ (solid content). The deodorant effects of the fibrous material thus obtained was evaluated. The results are shown in Table 6.

EXAMPLE 7

The same procedure was repeated as in Example 5, except that a T-cloth (138.9 g/m$^2$) was used as a fibrous substrate, thereby obtaining a deodorant fibrous material in which a porous polymer was combined with the fibrous substrate at the rate of 22 g/m$^2$ (solid content). The deodorant effects of the fibrous material thus obtained was evaluated. The results are shown in Table 6.

Comparative Example 2

The same procedure was repeated as in Example 5, except that 150 g of active carbon was used instead of the deodorant fibrous material. The results of the deodorant tests are shown in Table 6.

TABLE 6

| Example No. (fibrous material) | Rate of odor substance adsorption (%) | | |
|---|---|---|---|
| | Trimethylamine | Ammonia | Isovaleric acid |
| Example 5 (cuprammonium rayon) | 99.8 | 96.6 | 84.9 |
| Example 6 (polyester) | 96.1 | 92.9 | 80.7 |
| Example 7 (T-cloth) | 99.1 | 94.8 | 80.5 |
| Comparative Example 2[1] | 3.0 | 15.4 | — |

[1] Active carbon particles were used as a deodorant material.

It is understood that various other modifications will be apparent to and can readily be made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A deodorant porous polymer in the shape of substantially uniform particulates or an aggregate thereof, produced by the process of
    (a) mixing a solvent with of at least one alkoxide selected from the group consisting of inorganic alkoxides and metal alkoxides to form a sol-mixture;
    (b) optionally adding an acid catalyst;
    (c) adding a base catalyst to cause gelation; then
    (d) forming substantially uniform particulates by spray drying or freeze drying the sol-mixture.

2. A deodorant porous polymer in the shape of substantially uniform particulates or an aggregate thereof produced by the process of
    (a) mixing a solvent with of at least one alkoxide selected from the group consisting of inorganic alkoxides and metal alkoxides to form a sol-mixture;
    (b) optionally adding an acid catalyst;
    (c) adding a base catalyst to cause gelation;
    (d) grinding and heating the product of step (c) to form substantially uniform particulates.

3. A deodorant porous polymer film produced by the process of
    (a) mixing a solvent with of at least one alkoxide selected from the group consisting of inorganic alkoxides and metal alkoxides to form a sol-mixture;
    (b) optionally adding an acid catalyst;
    (c) adding a base catalyst to cause gelation;
    (d) forming the sol-mixture of step (a) into a film; then
    (e) drying the film to remove the solvent.

* * * * *